(12) United States Patent
Usman et al.

(10) Patent No.: US 6,713,456 B1
(45) Date of Patent: *Mar. 30, 2004

(54) NUCLEOZYMES

(75) Inventors: Nassim Usman, Boston, MA (US);
Robert J. Cedergren, Montreal (CA);
Jean-Pierre Perreault, Rawdon (CA);
Jing-Hua Yang, Montreal (CA);
Alexander Rich, Cambridge, MA (US)

(73) Assignees: Massachusetts Institute of Technology, Cambridge, MA (US); University of Montreal, Montreal (CA)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/459,340

(22) Filed: Jun. 2, 1995

Related U.S. Application Data (62) Division of application No. 07/829,729, filed on Jan. 31, 1992, now Pat. No. 5,652,094.

(51) Int. Cl.[7] .......................... A61K 48/00; C07H 21/04; C12Q 1/68; C12P 19/34
(52) U.S. Cl. ................... 514/44; 435/6; 435/91.3; 536/23.2; 536/24.5
(58) Field of Search ..................... 435/6, 91.31, 172.3, 435/32.01, 240.2; 536/23.1, 23.2, 24.5; 514/44

(56) References Cited

U.S. PATENT DOCUMENTS

| | | | |
|---|---|---|---|
| 5,149,796 A | | 9/1992 | Rossi et al. |
| 5,298,612 A | * | 3/1994 | Jennings .................... 536/23.2 |
| 5,334,711 A | | 8/1994 | Sproat et al. |

FOREIGN PATENT DOCUMENTS

| | | |
|---|---|---|
| WO | 8804300 | 6/1988 |
| WO | 9103162 | 3/1991 |
| WO | 9207065 | 4/1992 |

OTHER PUBLICATIONS

Roach TIBS 23:45–50, 1998.*
Stull et al. Pharm. Res. 1 2:465 (1995).*
Bass and Cech, "Ribozyme Inhibitors: Deoxyguanosine and Dideoxyguanosine are Competitive Inhibitors of Self–Splicing of the *Tetrahymena* Ribosomal Ribonucleic Acid Precusor," Biochemistry 25:4473–4477 (1986).
Been and Cech, "One Binding Site Determines Sequence Specificity of Tetrahymena Pre–rRNA Self Splicing, Trans–Splicing and RNA Enzyme Activity," *Cell* 47:207–216 (1986).
Cech, "A Model for the RNA–Catalyzed Replication of RNA," *Proc. Natl. Acad. Sci. USA* 83:4360–4363 (1986).
Cech, "RNA as an Enzyme," *Scientific American* 255:76–84 (1986).
Cech, "The Chemistry of Self–Splicing RNA and RNA Enzymes," *Science* 236:1532–1539 (1987).
Cedergren et al., "Catalytic RNA as an Anti–HIV Agent: Design and Delivery to Cells," *Abstract NIH Conference* Oct. 21–24 1990, San Diego, California.
Cedergren et al., Abstract presentation at Cold Spring Harbor meeting: RNA Processing, May 16–20, 1990.
Cedergren et al., Abstract presentation at Cold Spring Harbor meeting: RNA Processing, May 15–19, 1991.
Chowrira et al., "Four Ribose 2'–Hydroxyl Groups Essential for Catalytic Function of the Hairpin Ribozyme," *J. Biol. Chem.* 268:19458–19462 (1993).
Chowrira and Burke, "Binding and Cleavage of Nucleic Acids by the "Hairpin" Ribozyme," *Biochemistry* 30:8518 (1991).
Doudna et al., "A Multisubunit that is a Catalyst of and Template for Complementary Strand RNA Synthesis," *Science* 251:1605 (1991).
Engli et al., "Crystal Structure of an Okazaki Fragment at 2–A Resolution," *Proc. Natl. Acad. Sci. USA* 89:534–538 (1992).
Nielsen et al., "Sequence–Selective Recognition of DNA by Strand Displacement with a Thymine–Substituted Polyamide," *Science* 254:1497 (1991).
Paolella et al., "Nuclease Resistant Ribozymes with High Catalytic Activity," *EMBO Journal* 11:1913–1919 (1992).
Perreault et al., "Relationship between 2'–Hydroxyls and Magensium Binding in the Hammerhead RNA Domain: A Model for Ribozyme Catalysis," *Biochemistry* 30:4020–4025 (1991).
Perreault et al., "Mixed Deoxyribo– and Ribo–Oligonucleotides with Catalytic Activity," *Nature* 344:565–567 (1990).
Pieken et al., "Influence of 2'–Amino and 2'–Fluoro Modificaitons on the Catalytic Properties of Hammerhead Ribozymes," *Abstract of the 14th International tRNA workshop* May 4–9, 1991, Ridzyna, Poland.

(List continued on next page.)

*Primary Examiner*—Karen Lacourciere
(74) *Attorney, Agent, or Firm*—McDonnell Boehnen Hulbert & Berghoff (57) ABSTRACT

Nucleozymes containing ribonucleotides and deoxyribonucleotides or nucleic acid analogues are described herein. The nucleozymes have catalytic activity and are significantly more resistant to degradation than their all-RNA ribozyme counterparts. Also described are methods for preparing the nucleozymes along with methods of using nucleozymes, e.g., as therapeutic agents.

4 Claims, 5 Drawing Sheets

OTHER PUBLICATIONS

Pieken et al., "Kinetic Characterization of Ribonuclease–Resistant 2'–Modified Hammerhead Ribozymes," *Science* 253:314–317 (1991).

Price et al., "Inhibition of the Replication of Hepatitis B Virus by the Carbocyclic Analogue of 2'–deoxyguanosine," *Proc. Natl. Acad. Sci. USA* 86:8541–8544 (1989).

Scaringe et al., "Chemical synthesis of biologically active oligoribonucleotides using β–cyanoethyl protected ribonucleoside phosphoramidites," *Nucl Acids Res.* 18:5433–5441 (1990).

Strobel and Cech, "Tertiary Interactions with the Internal Guide Sequence Mediate Docking of the P1 Helix into the Catalytic Core of the T. Ribozyme," *Biochemistry* 32:13593 (1993).

Uhlenbeck, "A Small Catalytic Oligoribonucleotide," *Nature* 328:596–600 (1987).

Uhlmann and Peyman, "Antisense Oligonucleotides: A New Therapeutic Principle," *Chemical Reviews* 90:544–584 (1990).

Williams et al., "Properties of 2'–Fluorothymidine–Containing Oloigonucleotides: Interaction with Restriction Endonuclease EcoRV," *Biochemistry* 30:4001–4009 (1991).

Wu et al., "Convenient Procedure for the Preparation of Specific Mixed DNA–RNA Polymers," *J. Am. Chem. Soc.* 111:8531–8533 (1991).

Yang et al., "Mixed DNA/RNA Polymers Are Cleaved by the Hammerhead Ribozyme," *Biochemistry* 29:1156–11160 (1990).

Yang et al., "Minimum Ribonucleotide Requirement for Catalysis by the RNA Hammerhead Domain," *Biochemistry* 31:5005–5009 (1992).

Zaug and Cech, "The Intervening Sequence RNA to *Tetrahymena* Is a Enzyme," *Science* 231:470–475 (1986).

Zaug et al., "The Tetrahymena Ribozyme Acts Like an RNA Restriction Endonuclease," *Nature* 324:429434 (1986).

Zaug et al., "A Labile Phosphodiester Bond at the Ligation Junction in a Circular Intervening Sequence RNA," *Science* 224:574–578 (1984).

* cited by examiner

FIGURE 1A

| | POSITION OF RIBONUCLEOTIDE | | |
|---|---|---|---|
| | $rG^9rA^{10}$ | $rG^{12}rA^{13}$ | $rA^{28}rA^{29}rG^{30}$ |
| NEUCLEOZYME | | | |
| SEQ ID NO: 3  DR2R | rG | rA | -- |
| SEQ ID NO: 4  DR3R | rG | rA | rA |
| SEQ ID NO: 5  DR4R1 | rG | rA | rArG |
| SEQ ID NO: 6  DR4R2 | rG | rGrA | rG |
| SEQ ID NO: 7  DR4R3 | rG | rGrA | rA |
| SEQ ID NO: 8  DR5R2 | rG | rGrA | rArG |
| SEQ ID NO: 9  DR5R3 | rGrA | rGrA | rG |
| SEQ ID NO: 10 DR6R2 | rGrA | rGrA | rArG |
| SEQ ID NO: 2  DR7R | rGrA | rGrA | rArArG |
| OMe-NUCLEOZYME | | | |
| SEQ ID NO: 11 MR2R | rG | rG | -- |
| SEQ ID NO: 12 MR3R | rG | rA | rA |
| SEQ ID NO: 13 MR5R | rG | rGrA | rArG |

NUCLEOZYMES

RELATED APPLICATION

This application is a divisional of application Ser. No. 07/829,729, now U.S. Pat. No. 5,652,094, by Usman et al., filed Jan. 31, 1992, entitled "Nucleozymes," the whole of which is hereby incorporated by reference.

This invention was made with government support under grant Numbers NGR-22-009-277 awarded by NASA, and NIH-R37-CA04186 awarded by NIH. The government has certain rights in the invention.

FIELD OF THE INVENTION

This invention relates to nucleozymes, mixed nucleic acid polymers having catalytic activity. The invention also relates to methods of preparing and using nucleozymes.

BACKGROUND OF THE INVENTION

Proteins were the only known catalysts of cellular reactions until the discovery of RNA catalysts (ribozymes). In some instances, the folded structure of a ribozyme catalyses a cleavage reaction on another part of the same molecule (cis-reaction). In other instances (trans-reaction), the ribozyme may also act as a catalyst on another RNA or DNA molecule (substrate) by cleaving or ligating pieces of the substrate without changing itself in the process. (Zaug et al. Science, Vol. 231, pp. 470–75, 1986; Cech Science, Vol. 236, pp. 1532–39, 1987).

A well-characterized example of a ribozyme is the self-splicing Group I intron from the nuclear rRNA of Tetrahymena thermophila. An intron is an intervening sequence in a eukaryotic gene which does not encode a protein or in rare cases encodes a different protein. Introns are transcribed along with coding sequences (exons) to produce precursor RNA. The introns are removed from the precursor RNA and the exons are ligated by RNA cleaving and splicing steps. The Group I intron or ribozyme of T. thermophila catalyzes its own removal from the precursor RNA molecule. (Kruger et al. Cell 31:147–157, (1982); Zaug et al. (1986)). The self-splicing ribozyme catalyzes a variety of phosphodiester transfer reactions. The ribozyme can act as a ribonuclease, ligase, phosphotransferase, acid phosphatase, polymerase and RNA restriction endonuclease (Zaug, A. J., et al., Science 231:470–475 (1986); Zaug, A. J., et al., Nature 324:429–433 (1986); Zaug, A. J., et al., Biochemistry 25:4478–4482 (1986); Been, M. D., et al., Science 239:1412–1416 (1988); Doudna et al., Nature 339:519–522 (1989); all incorporated by reference herein).

The "hammerhead" and "hairpin" ribozymes also have been studied and described (Perreault et al., Nature 344:565–567 (1990); Perreault et al. Biochemistry 30:4020–25 (1991); Yang et al. Biochemistry 29:11156–60 (1990); Chowrira et al. Biochemistry 30:8518–22 (1991); Uhlenbeck Nature, 328:596–600 (1987)). The hammerhead ribozyme forms a stem loop secondary structure to form the catalytically active molecule. The hairpin ribozyme has a structure resembling a hairpin.

Although ribozymes are intriguing molecules, their use for in vivo applications is limited if not precluded. The all-RNA molecules are susceptible to degradation from enzymes (RNAses) present in vivo. There presently is no way known to inventors for delivering such molecules to the intended site in an active form.

SUMMARY OF THE INVENTION

The present invention is based on the discovery that ribozymes have catalytically critical sites and that it is not necessary to have an all-RNA molecule to have catalytic activity. The ribozyme like molecules of the invention or "nucleozymes" have ribonucleotides or nucleic acid analogues (hereinafter NAAs) at catalytically critical sites and NAAs or deoxyribonucleotides at non-catalytically critical sites. The preferred nucleozymes have ribonucleotides at catalytically critical sites. Nucleozymes have catalytic activity on the same substrates as their ribozyme counterparts.

The nucleozymes of the present invention thus essentially are modified ribozymes having at least a portion, or all, of the ribonucleotides replaced with deoxyribonucleotides or NAAs. The nucleozymes are significantly more resistant to degradation than their all-RNA ribozyme counterparts because the chemicals or enzymes present in vivo do not recognize the nucleic acid internucleotide bonds. The resistance can be to either enzymatic or chemical degradation. Preferably, a majority of the ribonucleotides of the ribozyme are replaced with deoxyribonucleotides or NAAs. The stability of the nucleozymes allows them to be useful as therapeutic agents whereas ribozymes would be cleaved and rendered inactive by enzymes, e.g. RNAses, present in vivo.

The nucleozymes of the present invention are chimeric nucleic acid polymers having catalytic activity due to and preferably optimized by the presence of RNA or a NAA at a catalytically critical site. The present invention provides chemistry which allows synthesis of the chimeric polymers and the determination of catalytically critical sites. The sites may be determined by varying the location of deoxyribonucleotides in a chimeric polymer and determining the locations responsible for or related to the chimeric polymer's ability to catalyze.

The present invention also pertains to a method for making a chimeric polymer. The polymers are made by phosphitylating protected ribonucleotides or NAAs units under conditions to form substantially pure-protected phosphoramidites or synthons of a single isomer. The protected phosphoramidites are coupled to each other forming a protected chimeric nucleic acid chain. The protecting groups are removed from the chimeric nucleic acid chain under conditions which completely deprotect the polymer.

The method of the present invention alleviates problems associated with a known prior art method for preparing chimeric RNA/DNA polymers (Perreault et al. Nature 344:565–567 (1990); Wu et al. Journal of the American Chemical Society 111:8531–33 (1989)). The prior art synthetic method for making chimeric polymers had problems with the migration of the protecting groups during the phosphitylating step, difficulty in removing the protecting groups and also has problems resulting from the process of removing the protecting groups in the deprotection step. The former problem results in the production of monomer units having protecting groups in an undesired position. The latter problem results, in many cases, in a) nucleotide modification, b) phosphodiester linkage isomerization, and c) to retention of a substantial amount of protecting groups on the polymer resulting in a non-functional polymer. The first problem was overcome in the present invention by selecting a catalyst capable of minimizing migration of protecting groups, e.g., a combination of 2,4,6-collidine and N-methylimidazole. The problem in removing the protecting groups was eliminated by deprotecting the mixed polymer in the presence of ethanolic ammonia.

The present invention also pertains to methods of using the nucleozymes. The nucleozymes may be used to perform the same catalytic functions as their all-RNA ribozyme counterparts. For example, a nucleozyme may be used as a ribonuclease, ligase, phosphotransferase, acid phosphatase, polymerase, or an RNA restriction endonuclease. The nucleozymes may be used to selectively cleave and ligate substrates by contacting the substrates with a nucleozyme such that the nucleozyme targets a specific sequence in the substrate for cleavage or ligation. The nucleozymes may be used as polymerases to polymerize the production of an oligoribonucleotide or an oligodeoxyribonucleotide. The nucleozymes also may be used in place of antisense RNA technology.

The nucleozymes also may be used as therapeutic agents introduced in vivo due to their resistance to chemical and enzymatic degradation. The nucleozymes may be used, for example, in a method for treating a subject for a retrovirus associated disease, e.g., human immunodeficiency virus (HIV). The method involves administering a therapeutically effective amount of at least one nucleozyme to the subject such that the nucleozyme cleaves the RNA genome of the retrovirus rendering it inactive. A plurality of nucleozymes also may be administered if it is desirable to target more than one sequence in the RNA genome.

A nucleozyme may be provided in a pharmaceutical composition. The pharmaceutical composition would include at least one nucleozyme and a pharmaceutically acceptable carrier.

It is an object of the present invention to provide a nucleozyme capable of maintaining its catalytic properties in vivo.

It is an object of the present invention to provide a chimeric nucleic acid polymer having catalytic activity.

It is yet another object of the present invention to provide a method for preparing chimeric polymers which are free of protecting groups and undesired isomeric side products.

It is yet another object of the present invention to provide a homogenous chimeric polymer.

DETAILED DESCRIPTION

The nucleozymes of the present invention have catalytic activity. Nucleozymes essentially are modified ribozymes preferably having at least one ribonucleotide or nucleic acid analogue (NAA) at a catalytically critical site(s) and deoxyribonucleotides or NAAs at non-critical sites. The term "nucleozyme" is intended to include catalytic chimeric polymeric chains containing ribonucleotides and deoxyribonucleotides and/or nucleic acid analogues.

A ribozyme is an all-RNA containing molecule capable of being a biological catalyst. Ribozymes are art recognized and examples of such molecules include the "hammerhead" or "hairpin" ribozymes.

The term "catalytic activity" is intended to include many types of catalysis. For example, the catalytic activity could be that of a ribonuclease, ligase, phosphotransferase acid, phosphatase, polymerase, and RNA restriction endonuclease.

The term "nucleic acid analogue" (NAA) is intended to include analogues which are structurally similar to ribonucleotides or deoxyribonucleotides and are capable of being monomer units in a polymer capable of hybridizing with DNA or RNA. The analogue may impart properties to a polymeric chain which differ from those of a nucleotide but the analogue is capable of being a monomer unit in a polymeric chain. The NAA may impart resistance to chemical or enzymatic degradation to the chimeric polymer. NAAs may be selected for their structural conformation if a particular conformation is desired for the polymer. A NAA which is structurally similar to a ribonucleotide may be positioned at a catalytically site if the NAA is capable of participating and/or attaining the desired catalytic activity. Preferably, if the NAA is positioned at a catalytically critical site it has a formula as depicted in Formulas I–IV below wherein X is a good coordinating ligand with divalent metal ions, eg., $Mg^{+2}$.

A nucleotide analogue may contain a heterocyclic ring as depicted in the formulae I–IV below or may be acyclic as shown in Formula V below. The preferred heterocyclic ring containing analogues of the present invention have three hydroxy substituents, alkoxy substituents or combinations thereof.

Formula (I)

Forumula (II)

Formula (III)

Formula (V)

-continued

Formula (IV)

In the above formulae, B is a base. The base nay be substituted or unsubstituted. Examples of bases include adenine, cytosine, guanine, uracil, 2-aminopurine, hypoxanthine, imidazole, $R_1$—SH—, and $R_1$—$NH_2$—. The term "base" is art-recognized and one of ordinary skill in the art would know which bases are useful in the present invention. X is selected from the group consisting of —$OR_1$, F, —$R_2OH$, —$NH_2$, —$R_2NH_2$, —Br, —$R_2Br$ and —$R_2F$ wherein $R_1$ is a lower alkyl group and $R_2$-$R_4$ are a lower alkyl hydrocarbon chains. The term "lower alkyl" is intended to include from one to six carbons, more preferably one to three carbons and most preferably a single carbon atom. For example, the most preferred X is methoxy.

B may be protected during the synthesis process. The protecting groups may be the conventional groups typically used in oligonucleotide synthesis processes e.g., $N^6$-benzoyl for adenine, $N^4$-benzoyl for cytosine, $N^2$-isobutyryl for guanine, and $N^2$-benzoyl for 2-aminopurine. Other useful protecting groups include phenoxyacetyl (PAC) and t-butoxyacetyl (TAC). One of ordinary skill in the art would know which protecting groups are appropriate for a particular base.

The NAAs capable of being positioned at a catalytically critical site may be determined by one of ordinary skill in the art using the following screening process. The catalytically critical sites of a particular ribozyme may be determined by positioning deoxyribonucleotides(s) at various locations within the ribozyme and evaluating the chimeric polymer's catalytic activity. After determining the locations of the catalytically critical sites, NAAs may be substituted for the deoxyribonucleotide(s) and the chimeric polymer's catalytic activity is again evaluated. If the NAA containing chimeric polymer possesses catalytic activity then the NAA is suitable for positioning at a catalytically critical site.

The term "synthon" is intended to include the fully protected monomer units (phosphoramidites) used to assemble the nucleic acid analogues of a chimeric polymer chain. The term "nucleic acid analogue" is used to describe the units when polymerized as part of a chimeric polymer chain.

The term "chimeric polymer" is intended to include polymers containing at least two different types of monomer units, e.g., RNA, DNA, or NAA. For example, a chimeric polymer may include RNA/DNA, RNA/NAA, or DNA/NAA polymeric chains. It should be understood that the linkages between the building units of the polymeric chain may be linkages capable of bridging the units together for either in vitro or in vivo. For example, the linkage may be a phosphorous containing linkage, e.g., phosphodiester or phosphothioate, or may be a nitrogen containing linkage, e.g., amide. It should further be understood that the chimeric polymer may contain non-nucleotide spacer molecules along with its other nucleotide or analogue units. Examples of spacer molecules which may be used are described in Nielsen et al. *Science*, 254:1497–1500 (1991), the contents of which are expressly incorporated by reference.

The analogues described above may be prepared using synthetic methods capable of attaching the desired moieties at the selected positions. Other possible analogues will be apparent to one of ordinary skill in the art. Deoxyribonucleotides are readily available and may be purchased from a variety of sources. The alkyl substituted heterocyclic ring containing analogues may be synthesized by first reacting the moiety being modified with arabino triflates (trifluoromethane sulfonates) and second displacing the arabino triflates with an appropriate organotin compound selected on the basis of the desired moiety. A schematic of this reaction is depicted below:

This synthesis scheme may be used to prepare analogues wherein X is selected from the group consisting of —$OR_1$, —$R_2OH$, $R_2F$, —RBr, and —$RNH_2$. One of ordinary skill in the art would know how to synthesis the halogenated analogues (X is —F or —Br) and the amino substituted analogues (X is —$NH_2$). These analogues may be synthesized as described by Williams et al., *Biochemistry*, 30:4001–4009 (1991), Doerr et al., *J. Org. Chem.*, 32:1462 (1967), Mengel et al. *Angew. Chem.*, 90:557 (1978), or Coddington et al., *J. Org. Chem.*, 29:558 (1964), the contents of each of the references are hereby expressly incorporated by reference.

The acyclic nucleic acid analogues may be prepared by reacting a protected acyclic molecule with a diol. Reaction processes which may be used are described in Durand et al., *Nucleic Acid Research*, 18:6353 (1990); Seela et al., *Nucleic Acid Research*, 15:3113–3124 (1987); Cload et al., *JACF*, 113:6324–6326 (1991), the contents of each reference is hereby expressly incorporated by reference.

Figure 1A:
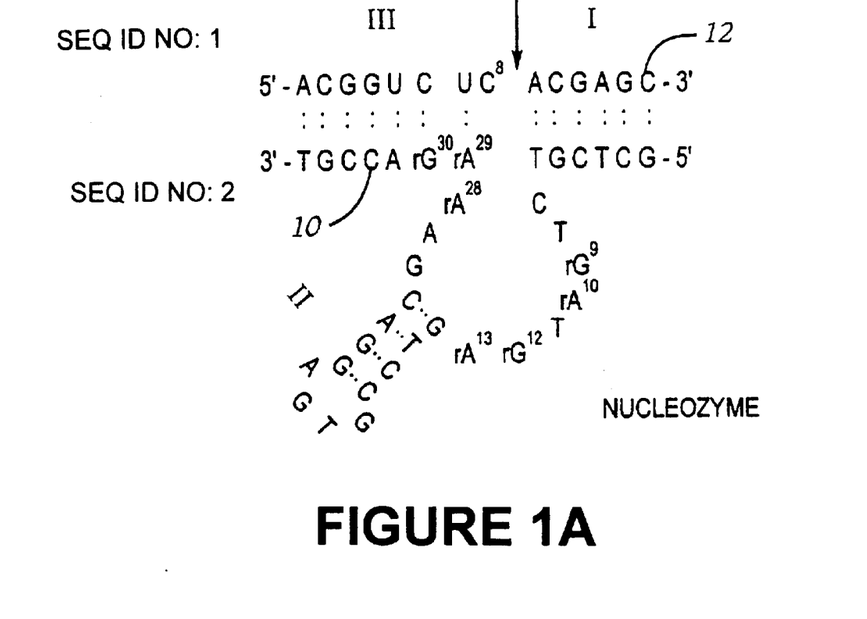
FIG. 1A depicts a structure of a hammerhead nucleozyme.
Figure 1B:
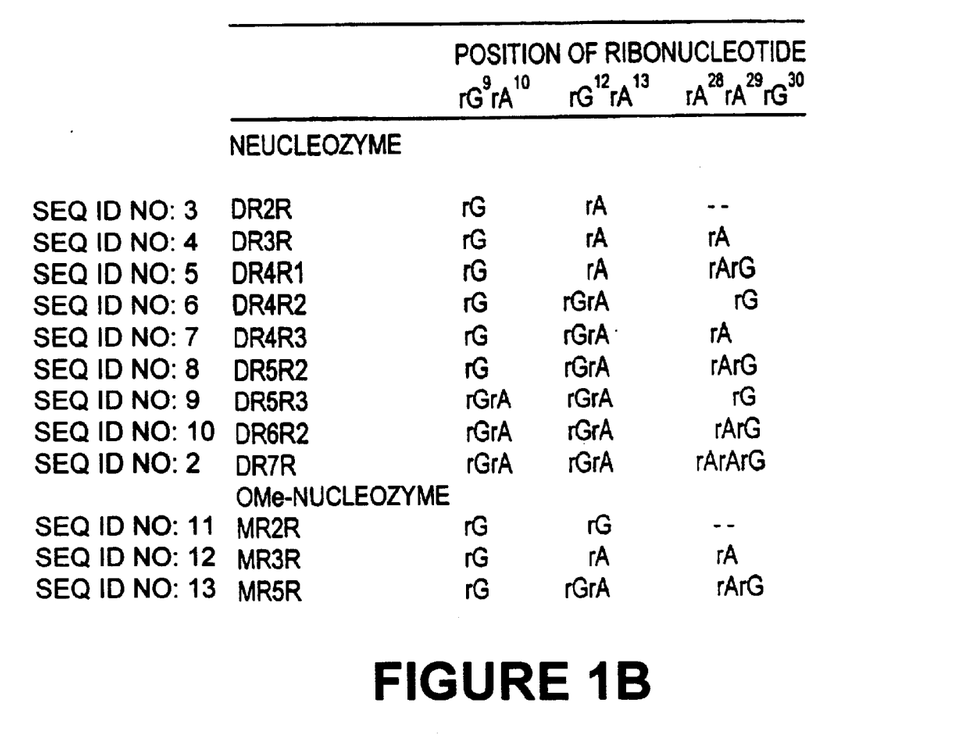
FIG. 1B is a table listing nucleozymes of the present invention indicating the positions of ribonucleotides in the nucleozymes. The position designations correspond to the structure depicted in FIG. 1A.

The nucleozymes have catalytically critical site(s) at which a ribonucleotide or NAA is necessary for the nucleozyme to have the desired level of catalytic activity. The term "catalytically critical site" is intended to include sites which, if altered from a ribonucleotide or a NAA to a deoxyribonucleotide, substantially reduces or even eliminates catalytic activity. A substantial reduction in catalytic activity would be that reduction which limits the usefulness of the nucleozyme as a catalyst in vitro or in vivo. The catalytically critical sites may be determined for each nucleozyme. Catalytically critical sites can be determined by preparing a variety of chimeric polymers using the chemical techniques described herein and comparing the catalytic activity of the chimeric test polymers. The catalytically critical sites in the all-RNA containing ribozyme counterparts are determined by selecting sites believed to be involved in catalysis and inserting a deoxyribonucleotide at the particular site. If the chimeric polymer does not have the same or substantially the same catalytic activity as the all-RNA counterpart, then the selected site is presumed to be a catalytically critical site. The hammerhead nucleozyme has four catalytically critical sites which are the G9, G12, A13 and A29 positions for the sequence depicted in FIG. 1.

The nucleozymes of the present invention are of a size capable of being synthesized using the chemistry described herein. Preferably, the nucleozymes have less than about 100 total building units, more preferably, less than about 80 building units, even more preferably, less than about 70 building units, and most preferably less than about 50 building units. Some nucleozymes may even have less than about 20 building units. The preferred nucleozyme is modeled after the hammerhead ribozyme, the catalytic portion of which has 35 building units. The term "building unit" is intended to include ribonucleotides, deoxyribonucleotides, or synthons.

The nucleozymes of the present invention are modified ribozymes having at least a portion of the ribonucleotides replaced with deoxyribonucleotides or NAAs. The modified ribozymes or nucleozymes are significantly more resistant to degradation than the all-RNA counterparts. The degradation may be either enzymatic or chemical degradation. The language "significantly more resistant to degradation" is that resistance which allows the nucleozyme to remain largely intact for an extended period of time relative to its all-RNA counterpart. Preferably it has a resistance which allows it to be administered for in vivo applications.

Figure 4A:
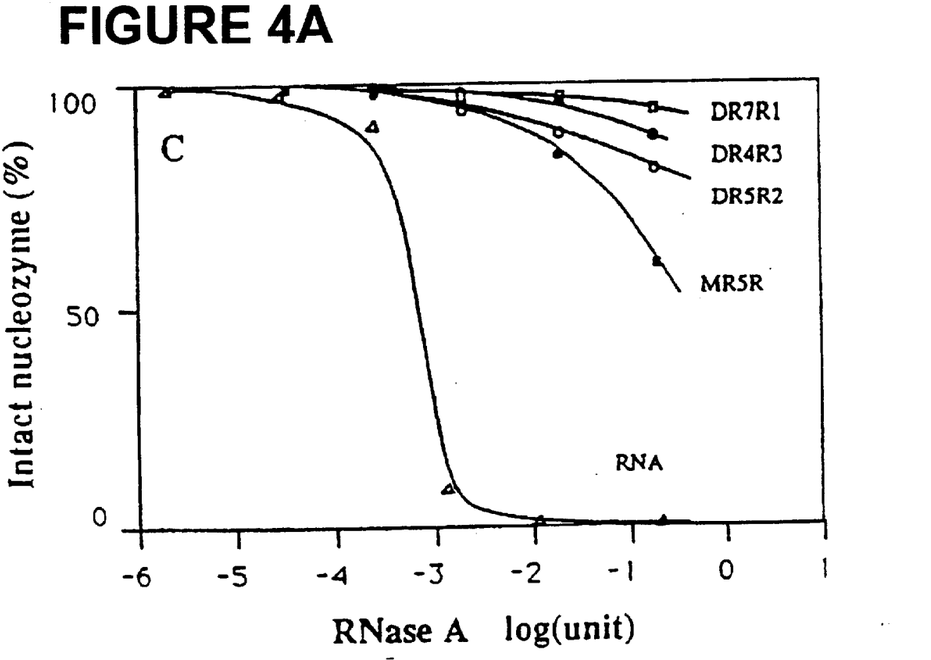
FIGS. 4A and 4B are graphs depicting the stability of nucleozymes compared to the stability of the all-RNA ribozyme counterpart after exposure to both RNAse A (4A) and a yeast cellular extract (4B).
Figure 4B:
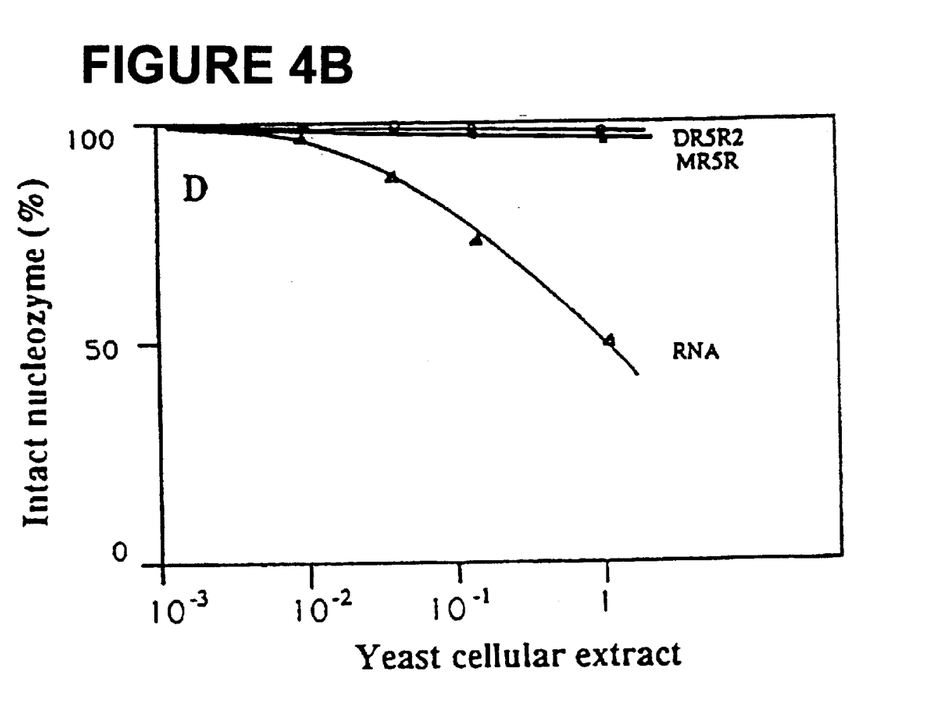

Resistance to enzymatic degradation may be resistance to enzymes present in vivo, e.g. RNAses such as RNAse A. FIGS. 4A and 4B are graphs depicting the relationship between the percentage of the nucleozyme being intact at a particular RNAse A (FIG. 4A) or yeast cellular extract (FIG. B) concentration. The data set forth in FIGS. 4A and 4B was obtained using the following procedure. A sample of 0.001 pmol of 5' labeled nucleozyme or ribozyme was incubated with 0.5 mg of carrier TRNA in 50 mM Tris-HCl (pH 7.4) and 10 mM $Mg^{+2}$ and different concentrations of RNAse A or yeast extract ten minutes for A, thirty minutes for extract. The reactions were stopped by the addition of 20 mM EDTA and loaded and analyzed on 15% PAGE in 7M urea. The yeast extract was prepared from a 1 ml culture of yeast strain BWG2-9A grown to late-lag phase, harvested and washed with 25 mM sodium phosphate buffer (pH 7.8). The pellet was suspended in 100 $\mu$l of the same buffer and sonicated for 20 seconds (60W). After centrifugation for five minutes in an Eppendorf centrifuge, the supernatant was used directly after appropriate dilutions and incubations with the nucleozymes and the all-RNA ribozyme.

As shown in FIG. 4A, the nucleozymes were at least about 75% intact at an RNAse A log concentration of −1.5 and at least about 80% intact at an RNAse A log concentration of −2.5. Preferably, the nucleozyme is at least about 90% intact at both concentrations. The difference in stability between the nucleozymes and ribozyme is even more apparent when the enzyme is a yeast cellular extract (FIG. 4B). The nucleozymes were at least 90% intact at all of the tested concentrations.

The chemical degradation for purposes of this invention is intended to include resistance to chemicals present in vivo and in vitro. The resistance may be to alkaline hydrolysis, e.g., sodium hydroxide and water.

The preferred nucleozymes of the present invention are modified ribozymes having a majority of the ribonucleotides replaced with deoxyribonucleotides or NAAs. At least one of the units is a deoxyribonucleotide and preferably most of the units are deoxyribonucleotides. The nucleozymes more preferably, have at least about 75%, even more preferably at least about 85%, most preferably at least about 90% of their ribonucleotides replaced with deoxyribonucleotides or NAAs. The nucleozyme also may be made up entirely of NAAs or a combination of NAAs and deoxyribonucleotides.

The present invention also pertains to a method of making a chimeric polymer. The method is similar to that described by Scaringe et al. to produce an all-RNA polymer. (*Nucleics Acid Research* Vol. 18, No. 18, 5433–41 (1990)), the contents of which is expressly incorporated by reference. The method includes the steps of phosphitylating protected RNA, DNA or NAA units under conditions which minimize migration of the protecting group forming isomerically pure protected phosphoramidites. The protected RNA or synthons may have the desired moieties protected with the protecting groups capable of surviving the phosphitylation and coupling steps. Examples of such groups include conventional DNA protecting groups such as 5'-O-DMT, N-Bz (Ade and Cyt), N-iBu (Gua), β-cyanoethyl for phosphate, TB DMS for 2'-hydroxyl.

The term "isomerically pure protected phosphoramidites" is intended to include phosphoramidite preparations free of a substantial amount of undesired isomers of the phosphoramidites. A substantial amount is that amount which would substantially interfere or impede with the preparation's ability to be used in forming a mixed polymeric chain. For example, a consideration in the chemical synthesis of a ribonucleotide phosphoramidite is contamination of the desired 2'-O-protecting group-3'-O phosphoramidite with the undesired 3'-O-protecting group-2'-O-phosphoramidite. Syntheses performed with the latter lead to oligonucleotides having 5'-2' linkages. Isomerically pure protected phosphoramidites of the present invention lead to oligonucleotides which are free of such undesired linkages.

The method of the present invention also involves coupling the protected phosphoramidites together forming a protected chimeric polymeric chain. The coupling can be done using well-known chemical techniques known to one of ordinary skill in the art. Preferably the coupling is done on an automated synthesizer.

After the chimeric polymeric chain is formed, the protecting groups now can be removed from the chain under conditions which completely deprotect the polymer. Also, nucleotide base modification and/or phosphodiester linkage isomerization of the chain now can be minimized during the deprotection step.

The prevention of migration of the protecting groups in the phosphitylation step can be accomplished by phosphitylating in the presence of a catalyst selected to minimize migration. An example of such a catalyst is the combination of 2,4,6-collidine and N-methylimidazole.

The invention permits removal of the protecting groups in a manner that is complete and that minimizes nucleotide base modification and/or phosphodiester linkage isomerization. Complete removal of protecting groups includes substantially complete removal where a polymeric chain may have a small number of protecting groups still attached which do not effect the polymeric chain's intended catalytic function. The deprotection step is accomplished by deprotecting the polymer in the presence of an agent capable of minimizing such effects. An example of such an agent is ethanolic ammonia.

The method also allows the production of a homogeneous RNA/DNA polymer free of undesired isomeric products. The term "free" is intended to include substantially free wherein a small amount of protecting groups or undesired isomers are present as long as the amount does not interfere or impede the polymer's function. The minimization of nucleotide base modification is intended to include that modification which would effect a polymeric chain's intended catalytic function. Minimizing phosphodiester linkage isomerization, when used in connection with a molecule, means preventing that degree of isomerization which would, adversely affect the molecule's intended catalytic function. Minimizing phosphodiester linkage isomerization when used in connection with a preparation, means preventing that degree of isomerization which would substantially affect the preparation's abilities to be used for its intended catalytic functions.

The present invention also pertains to methods for using the nucleozymes. The nucleozymes may be used for any method in which a ribozyme presently may be used. For example, the nucleozyme may be used to selectively cleave an RNA substrate or to ligate two pieces of RNA together. When cleaving a substrate, the RNA substrate is contacted with at least one nucleozyme which targets a specific sequence in the substrate for cleavage. A plurality of nucleozymes also may be used in a cleavage process.

The nucleozymes of the present invention also may be used to polymerize an oligonucleotide molecule. The oligonucleotide may contain ribonucleotides, deoxyribonucleotides, and analogues of deoxy- or ribonucleotides. A template is contacted with a population of the appropriate nucleotide monomer units and a nucleozyme under conditions which allow an oligonucleotide complementary to the template to form. The template preferably is attached to a support.

The nucleozymes of the present invention also may be used for therapeutic methods due to their stability in vivo. The nucleozymes may be used, for example, to treat a subject for a retrovirus associated disease. A therapeutically effective amount of at least one nucleozyme is administered to a subject such that the nucleozyme(s) cleaves the RNA genome of the retrovirus or the viral mRNA rendering it inactive.

A retrovirus associated disease is intended to include diseases involving retroviruses. Retroviruses have an RNA genome making them susceptible to cleavage by the at least one nucleozyme or the plurality of nucleozymes. An example of such a retrovirus associated disease is AIDS wherein the causative retrovirus is the human immunodeficiency virus (HIV).

The term "subject" is intended to include living organisms susceptible to retroviruses, e.g., mammals. Examples of subjects include humans, cats, and rats.

The language "therapeutically effective amount" is intended to include that amount capable of eliminating or significantly reducing the symptoms associated with retrovirus associated diseases. The amount may be determined on an individual basis and will be based, at least in part, on consideration of the severity of symptoms to be treated, the results sought and the size of the subject. Thus, a therapeutically effective amount may be determined by one of ordinary skill in the art employing such factors using no more than routine experimentation.

The nucleozymes of the present invention also may be used in conjunction with or in place of antisense RNA technology. That is, to control the expression of a gene by targeting an appropriate mRNA. A nucleozyme may be selected based on its ability to target a particular mRNA sequence and subsequently an effective amount of the nucleozyme may be administered to a subject. The effective amount would be that amount necessary to target the RNA and control expression of a selected gene.

The present invention also pertains to pharmaceutical compositions containing at least one nucleozyme and a pharmaceutically acceptable carrier. The language pharmaceutically acceptable carrier is intended to include carriers capable of being co-administered with the nucleozyme(s) while not adversely affecting the nucleozyme(s) catalytic activity. The carrier may be solid or liquid or a gel. Examples of liquid carriers include water, an aqueous solution of a non-toxic salt, e.g., sterile physiological saline solutions, or aqueous solutions containing organic solvents, e.g., ethanol. Also suitable are emulsions, such as oil-in-water. Solid carriers may include nutritive carriers, e.g., sucrose or gelatin, or non-nutritive carriers, e.g., cellulose or talc.

The Preferred Embodiment

The preferred nucleozymes of the present invention are modeled after the "hammerhead" ribozyme. The moderate size of the catalytic hammerhead domains of RNA lends itself to chemical synthesis. As shown in FIG. 1A, the conserved hammerhead domain of around fifty ribonucleotides found in naturally occurring RNA has been petitioned between a thirty-five unit catalytic fragment 10, the ribozyme, and a fourteen nucleotide substrate unit 12.

The all-DNA analog of the hammerhead domain is inactive in catalysis. It was determined that nucleozymes containing as few as four ribonucleotides out of a total of thirty five nucleotides have catalytic activity. Active hammerhead nucleozymes require the presence of ribonucleotides in particular at four positions, particular the G9, G12, A13, and A29 positions shown in FIG. 1B.

FIG. 1B is a table showing the chimeric polymers prepared along with the positions of ribonucleotides within the polymers. Nucleozymes are abbreviated as follows: DR and MR designate nucleozymes composed of predominantly deoxyribonucleotides and 2'-methoxynucleotides, respectively. The following number indicates the number of ribonucleotides and the final number refers to a particular combination of ribonucleotides.

Figure 2A:
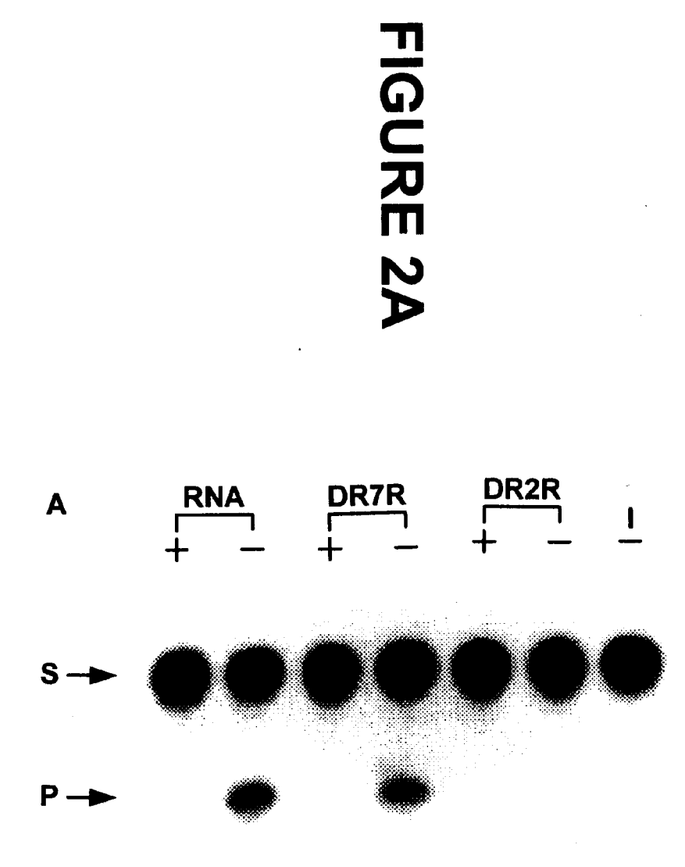
FIGS. 2A and 2B are photographs of a gel demonstrating the cleavage of a 5'-$^{32}$P-labeled RNA substrate. The designation "RNA" is the all-RNA containing ribozyme and the nucleozymes are as abbreviated in FIG. 1B.
Figure 2B:
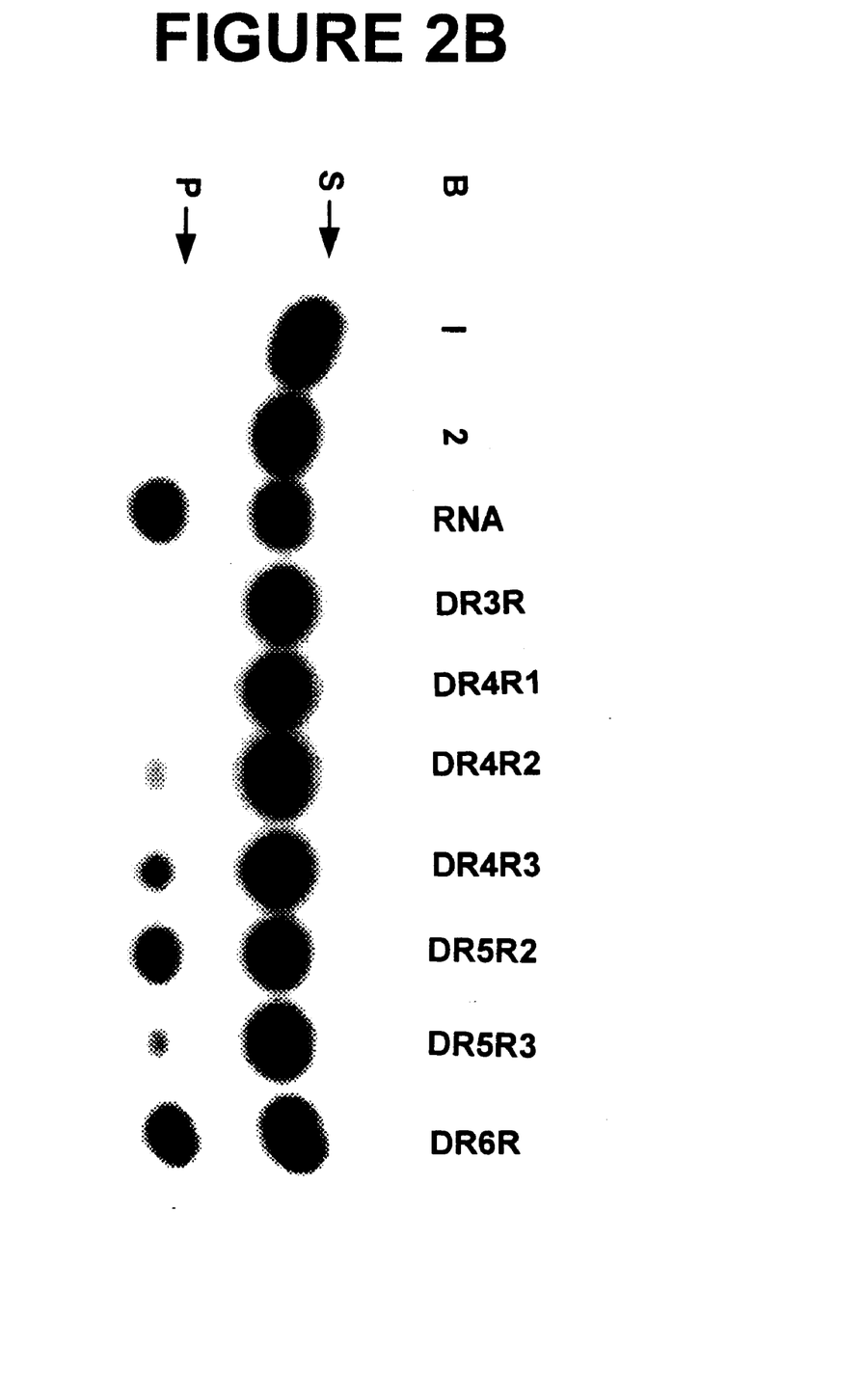

The all DNA analog of the hammerhead domain is inactive in catalysis. Several RNA/DNA mixed polymers appear as set forth and designated in the table of FIG. 1B. As shown in FIGS. 2A and 2B, the mixed polymer having ribonucleotides at positions 9, 10, 12, 13, 28, 29 and 30 of the ribozyme showed good catalytic activity (FIG. 2A). The nucleozyme containing the fewest ribonucleotides, DR4R3 and DR4R2, showed at least some activity. In FIGS. 2A and 2B, S indicates the mobility of the intact substrate and P, the product. RNA is the all-RNA ribozyme and nucleozymes are abbreviated as in FIG. 1A. The presence or absence of the enzymatic fragment is indicated by + or −, respectively in FIG. 2A. Lane 1 is a control lacking the added catalytic fragment in FIG. 2A. Lane 1 in FIG. 2B is the 4.5 hour incubation of the substrate with neither $Mg^{+2}$ nor nucleozyme and lane 2 is an incubation control in the presence of $Mg^{+2}$ but no added nucleozyme. The samples were analyzed on 15% PAGE in 7M urea.

Figure 3:
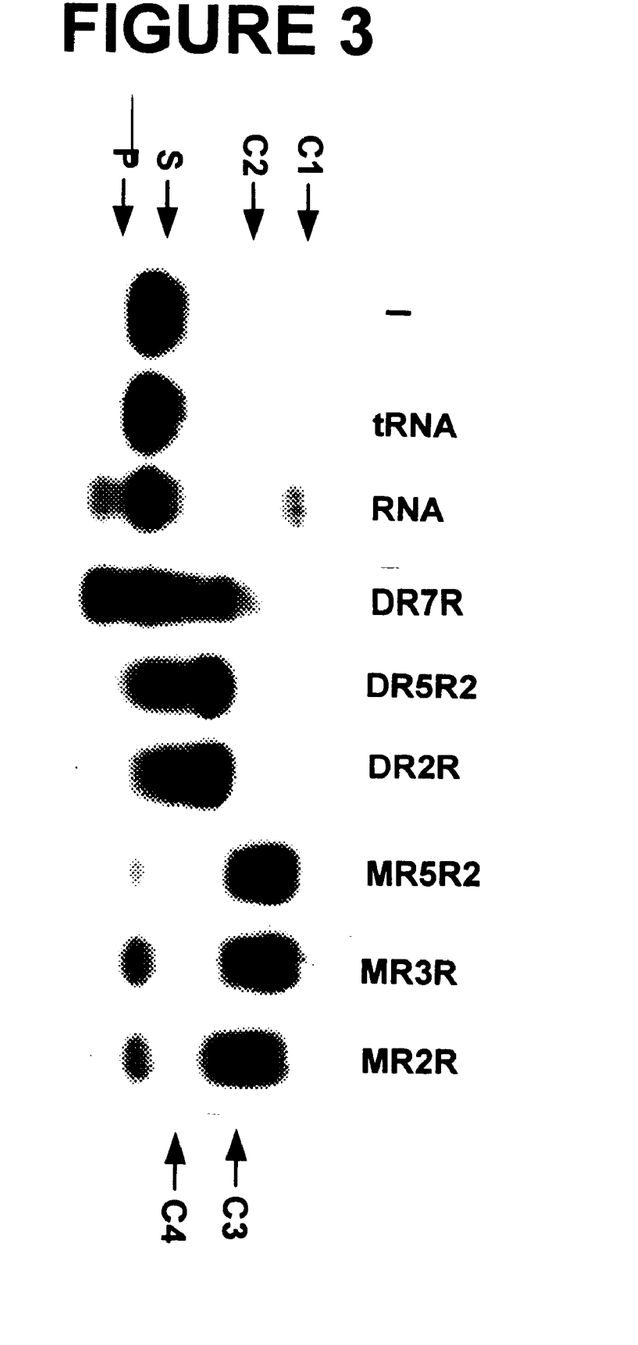
FIG. 3 is a photograph of a gel demonstrating the cleavage of a radioactive RNA substrate by nucleozymes of the present invention containing methoxy substituted NAAs. The nucleozymes are abbreviated as in FIG. 1B.

FIG. 3 is a photograph showing the cleavage of radioactive substrates by OMe-nucleozymes. The S indicates the mobility of the intact substrate and P, the product. The reactions were performed as in FIG. 2 except that the incubations of the substrate were with the MR5R nucleozyme, for four hours and the $(Mg^{+2})$ was varied. Lane 1 contained no $Mg^{+2}$, lane 2-10 mM, lane 3-20 mM, lane 4-30 mM and lane 5-50 mM. The OMe-nucleozymes are nucleozymes having synthons which are methoxysubstituted in the 2' position. The nucleozymes designated MR contain all methoxysubstituted nucleozymes rather than deoxyribonucleotides.

The catalytic activity of the nucleozymes was further evaluated by determining parameters including $K_M$ and $K_{cat}$ for some of the kinetic reactions. In addition, the $K_{Mg}$, $K_s$ and $k_3$ of nucleozyme reactions were obtained to evaluate how extensive deoxyribonucleotide substitution effects $Mg+^2$ cofactor binding. A summary of these results is presented in Table 1 below.

TABLE I

Kinetic parameters of nucleozyme-catalyzed reactions[a]

| Substrate/Nucleozyme | $K_M$ ($\mu M$) | Kcat (l/min) | $K_S$ ($\mu M$) | $K_3$ (l/min) | $K_{Mg}$ (mM) |
|---|---|---|---|---|---|
| RS/DR4R3 | 4.2 | 0.004 | 5 | 0.013 | 23 |
| RS/DR5R2 | 4.9 | 0.013 | 4 | 0.040 | 24 |
| RS/DR7R | 4.5 | 0.067 | 5 | 0.21 | 24 |
| RS/RR | 0.7 | 1.2 | 0.8 | 1.8 | 8.1 |

[a]The kinetic experiments were performed under the standard conditions of FIG. 2 with following differences: the final concentrations were: nucleozyme 0.05 $\mu M$; substrate from 0.5 $\mu M$ to 5 $\mu M$; $Mg^{2+}$ from 5 to 50 mM and the reaction times from 30 min to 6 h at 30° C. Initial rates were determined from the first 10% of the reactions. The chronology of substrate and metal ion addition is currently not known. The values for Ks, k3 and KMg were, therefore, determined from the following random assembly model for ternary complex formation:

The generalized reaction scheme used to determine the K values is depicted below.

The reaction scheme starts with the catalytic species, the substrate and the $Mg^{+2}$ cofactor, traversing a ternary complex and yielding a product. The apparent $K_m$'s and $K_s$s of the three nucleozymes are virtually identical and approximately five times those of the all-RNA ribozyme acting on an RNA substrate.

The chimeric polymers were synthesized as follows:
Ribonucleotide, Deoxyribonucleotide, or 2'-Methoxy Analogue Phosphoramidite Synthesis and Purification Dry N-Acyl-5 '-O-DMT-2'-O-sily-ribonucleoside (10 mmol, 1 eq) was dissolved in 30 ml dry THF in a 300 ml round bottom flask. 2,4,6-Collidine (75 mmol, 7.5 eq) was added followed by N-methylimidazole (5 mmol, 0.5 eq). (N,N-dispropylamino) (cyanoethyl) phosphonamidic chloride (20 mmol, 2.0 eq [22 mmol, 2.2 eq in the case of guanosine or other nucleotide bases with reactive lactams]) was then added dropwise over 5 min at room temperature. The reaction was clear at the start but a white precipitate formed within 3 min (this is the collidine hydrochloride salt). The reaction was complete after 1–2 hour (determined by TLC). The reaction was then placed in an ice bath and diluted with 100 ml (1 volume) ethyl acetate. 150 ml 5% $NaHCO_3$ was added slowly (the first 10 ml over 5 minutes). (In the case of guanosine the reaction was first quenched with 5 ml of absolute ethanol). Heat was generated by the quenching of excess phosphitylating reagent. The mixture was then transferred to a separatory funnel and a second volume of ethyl acetate (100 ml) was added after first rinsing out the reaction flask. The aqueous phase was removed and the organic phase washed with saturated NaCl. The combined aqueous washes were back extracted with 50 ml. ethyl acetate and the combined organic phases were dried over $Na_2SO_4$. The solvent was removed in vacuo yielding a viscous oil. Coevaporation (×5) with 50 ml toluene afforded the crude phosphoramidite as an offwhite foam or oil. Excess phosphinic acid and collidine caused it to be oily. After leaving the amidite under high vacuum overnight, resuspension and rotovaping of the amidite with methylene chloride and ethyl acetate usually produced a foam. The phosphoramidites were further purified by silica gel chromatography yielding a white foam in 75–85% yields. This procedure was repeated for the preparation of the other desired phosphoramidites changing the initial protected nucleotide unit. The phosphoramidites were used to synthesize the mixed polymers using automated synthesis techniques commonly used for the synthesis of deoxyribonucleotides.

Automated Synthesis of Mixed Polymers

All syntheses were conducted on either a Gene Assembler Plus (Pharmacia), or a Cyclone (Milligen/Biosearch) synthesizer using standard protocols with an extended 12 min coupling step. A 30 fold excess (150 $\mu l$ of 0.1 M=15 mg, ~15 $\mu mol$) of the phosphoramidites and a 400 fold excess of tetrazole (400 $\mu l$ of 0.5M=200 $\mu mol$) relative to CPG bound 5'-hydroxyl was used in each coupling cycle. Synthesis scale was 0.5 $\mu mol$. Average coupling yields on the Gene Assembler Plus, monitored by an on-line colorimeter, were ~99.0% and on the Cyclone 97–98%, determined by colorimetric quantitation of the trityl fractions. Reaction columns for 0.5 $\mu mol$ syntheses were Milligen/Biosearch 1.0 $\mu mol$ columns. Oligonucleotide synthesis reagents: 1) for GA plus: detritylation solution was 2% TCA in ethylene dichloride; capping was performed with 20% N-Methyl imidazoyl in THF and 10% acetic anhydride/10% 2,6-lutidine in THF; oxidation solution was 0.02 $MI_2$, 1% lutidine, 10% water in tHF. Baker Bio-Analyzed grade acetonitrile was further dried over activated 4 A molecular sieves. Tetrazole solution (0.5 M in acetonitrile was obtained from Applied Biosystems. 2) for Cyclone: all standard DNA synthesis ancillary reagents were used.

Deprotection of Mixed Polymers

The CPG-bound mixed polymer was transferred from the synthesis column to a 4 ml glass screw top vial. 1 ml of ethanolic ammonia was added and heated at 55° C. for 16 hr. After cooling to −20° C., the ethanolic ammonia was removed from the CPG beads and the CPG was washed with 0.5 ml of 50:50/ethanol:water which was-then added to the ethanolic ammonia. The combined supernatants containing the oligoribonucleotide were dried to a white powder. To remove the silyl protecting groups, the ammonia-deprotected mixed polymer was resuspended in 50 $\mu l$ of 50:50/ethanol:water and 600 $\mu l$ of 1M TBAF/THF and left at room temperature for about 24 hr. The solution was then added directly to 10 ml of 0.1M TEAB and loaded onto a Qiagen 500 anion exchange cartridge (Qiagen Inc., Studio City, Calif.) prewashed with 10 $\mu l$ of 0.5M TEAB, the nucleozyme was eluted with 7 ml of 2M TEAB and dried down to a white powder.

Gel Purification of Fully Deprotected Mixed Polymers

The oligomers were first checked by analytical PAGE (0.75 mm×20 cm×45 cm). 1 ODU of oligonucleotide in 5 $\mu l$ $H_2O$ was added to 5 $\mu l$ of deionized formamide and the total 10 $\mu l$ solution was loaded into a 1 cm wide lane. Following electrophoresis the gels were photographed by placing the gel over a fluorescent TLC plate and illuminating the gel with a UV lamp. The desired sequence was established according to electrophoretic mobility and purified by preparative electrophoresis using 1.5 mm thick gels with a single 12 cm wide lane. After electrophoresis the desired band was excised, crushed, placed into a sterile 5 ml test tube, and covered with 50 mM NH₄OAc pH 7.0. The tube was covered and kept at 37° C. O/N. The supernatant was then removed and the gel pieces washed with an additional 1 ml of the extraction buffer. The combined washings were filtered through a 0.45 micron filter and loaded onto a 1 gram size Sep-Pak C18 cartridge (Waters-Millipore) prewashed with 5 ml each of acetonitrile, 50% acetonitrile/0.1M TEAB and 0.1M TEAB. After washing the cartridge with 5 ml of 0.1 M TEAB, the RNA was eluted in 5 ml 35:35:30 acetonitrile/methanol/water and dried down to a white powder.

The mixed polymers set forth in the Table of FIG. 1B were prepared as described above.

EQUIVALENTS

Those skilled in the art will be able to ascertain, using no more than routine experimentation, many equivalents of the specific embodiments of the invention described herein.

These and all other equivalents are intended to be encompassed by the following claims.

What is claimed is:

1. A pharmaceutical composition, comprising:

at least one enzymatic nucleic acid molecule having a ribonucleotide at a catalytically critical site, at least one deoxyribonucleotide and at least one nucleic acid analog; and a pharmaceutically acceptable carrier.

2. The pharmaceutical composition of claim 1, wherein said enzymatic nucleic acid molecule has enzymatic activity to cleave a separate ribonucleic acid molecule, and comprises:

a nucleotide base-containing molecule having a hammerhead motif which has the formula 3'-V-W-X-Y-Z-5', wherein V and Z are sequences which can base pair with said separate ribonucleic acid molecule and X is a sequence which can base pair inter se to form a hairpin; and wherein W comprises 3'-$A^b$AAG-5', Y comprises two 3'-$AG^b$-5'; wherein b represents a nucleotide having a 2'-OH group;

and a pharmaceutically acceptable carrier.

3. A pharmaceutical composition, comprising:

at least one enzymatic nucleic acid molecule having a ribonucleotide at a catalytically critical site and at least one deoxyribonucleotide or nucleic acid analog and has enzymatic activity to cleave a separate ribonucleic acid molecule, comprising:

a nucleotide base-containing molecule having a hammerhead motif which has the formula 3'-V-W-X-Y-Z-5', wherein V and Z are sequences which can base pair with said separate ribonucleic acid molecule and X is a sequence which can base pair inter se to form a hairpin; and wherein W comprises 3'-$A^b$AAG-5, Y comprises two 3'-$AG^b$-5'; wherein b represents a nucleotide having a 2'-OH group; and wherein at least one of the sugar moieties in said enzymatic nucleic acid molecule comprises, at its 2'-position, an analogue group other than hydroxyl alone, wherein said analogue group is not 2'-alkoxy or 2'-halo, and does not comprise a nitrogen atom linked to the 2'-C, wherein said analogue group at each 2'-position may be the same or different;

and a pharmaceutically acceptable carrier.

4. A pharmaceutical composition, comprising:

at least one enzymatic nucleic acid molecule having a ribonucleotide at a catalytically critical site and at least one deoxyribonucleotide or nucleic acid analog, and has catalytic activity to cleave a separate ribonucleic acid molecule, wherein said enzymatic nucleic acid molecule comprises a nucleotide base-containing molecule having a hairpin motif; and a pharmaceutically acceptable carrier.

* * * * *

SEQUENCE LISTING

<160> NUMBER OF SEQ ID NOS: 13

<210> SEQ ID NO 1
<211> LENGTH: 14
<212> TYPE: RNA
<213> ORGANISM: Artificial
<220> FEATURE:
<223> OTHER INFORMATION: Example of a Nucleozyme target sequence

<400> SEQUENCE: 1
acggucucac gagc                                                      14

<210> SEQ ID NO 2
<211> LENGTH: 35
<212> TYPE: DNA
<213> ORGANISM: Artificial
<220> FEATURE:
<223> OTHER INFORMATION: Description of Artificial Sequence: Nucleozyme
<220> FEATURE:
<221> NAME/KEY: misc_feature
<222> LOCATION: (9)..(10)
<223> OTHER INFORMATION: Ribonucleotide
<220> FEATURE:
<221> NAME/KEY: misc_feature
<222> LOCATION: (12)..(13)
<223> OTHER INFORMATION: Ribonucleotide
<220> FEATURE:
<221> NAME/KEY: misc_feature
<222> LOCATION: (28)..(30)
<223> OTHER INFORMATION: Ribonucleotide

<400> SEQUENCE: 2
gctcgtctga tgagtccgtg aggacgaaag accgt                               35

<210> SEQ ID NO 3
<211> LENGTH: 35
<212> TYPE: DNA
<213> ORGANISM: Artificial
<220> FEATURE:
<223> OTHER INFORMATION: Description of Artificial Sequence: Nucleozyme
<220> FEATURE:
<221> NAME/KEY: misc_feature
<222> LOCATION: (9)..(9)
<223> OTHER INFORMATION: Ribonucleotide
<220> FEATURE:
<221> NAME/KEY: misc_feature
<222> LOCATION: (13)..(13)
<223> OTHER INFORMATION: Ribonucleotide

<400> SEQUENCE: 3
gctcgtctga tgagtccgtg aggacgaaag accgt                               35

<210> SEQ ID NO 4
<211> LENGTH: 35
<212> TYPE: DNA

```
<213> ORGANISM: Artificial
<220> FEATURE:
<223> OTHER INFORMATION: Description of Artificial Sequence: Nucleozyme
<220> FEATURE:
<221> NAME/KEY: misc_feature
<222> LOCATION: (9)..(9)
<223> OTHER INFORMATION: Ribonucleotide
<220> FEATURE:
<221> NAME/KEY: misc_feature
<222> LOCATION: (13)..(13)
<223> OTHER INFORMATION: Ribonucleotide
<220> FEATURE:
<221> NAME/KEY: misc_feature
<222> LOCATION: (29)..(29)
<223> OTHER INFORMATION: Ribonucleotide

<400> SEQUENCE: 4
gctcgtctga tgagtccgtg aggacgaaag accgt                              35

<210> SEQ ID NO 5
<211> LENGTH: 35
<212> TYPE: DNA
<213> ORGANISM: Artificial
<220> FEATURE:
<223> OTHER INFORMATION: Description of Artificial Sequence: Nucleozyme
<220> FEATURE:
<221> NAME/KEY: misc_feature
<222> LOCATION: (9)..(9)
<223> OTHER INFORMATION: Ribonucleotide
<220> FEATURE:
<221> NAME/KEY: misc_feature
<222> LOCATION: (13)..(13)
<223> OTHER INFORMATION: Ribonucleotide
<220> FEATURE:
<221> NAME/KEY: misc_feature
<222> LOCATION: (29)..(30)
<223> OTHER INFORMATION: Ribonucleotide

<400> SEQUENCE: 5
gctcgtctga tgagtccgtg aggacgaaag accgt                              35

<210> SEQ ID NO 6
<211> LENGTH: 35
<212> TYPE: DNA
<213> ORGANISM: Artificial
<220> FEATURE:
<223> OTHER INFORMATION: Description of Artificial Sequence: Nucleozyme
<220> FEATURE:
<221> NAME/KEY: misc_feature
<222> LOCATION: (9)..(9)
<223> OTHER INFORMATION: Ribonucleotide
<220> FEATURE:
<221> NAME/KEY: misc_feature
<222> LOCATION: (12)..(13)
<223> OTHER INFORMATION: Ribonucleotide
<220> FEATURE:
<221> NAME/KEY: misc_feature
<222> LOCATION: (30)..(30)
<223> OTHER INFORMATION: Ribonucleotide

<400> SEQUENCE: 6
gctcgtctga tgagtccgtg aggacgaaag accgt                              35

<210> SEQ ID NO 7
<211> LENGTH: 35
<212> TYPE: DNA
<213> ORGANISM: Artificial
<220> FEATURE:
<223> OTHER INFORMATION: Description of Artificial Sequence: Nucleozyme
<220> FEATURE:
<221> NAME/KEY: misc_feature
<222> LOCATION: (9)..(9)
<223> OTHER INFORMATION: Ribonucleotide
```

```
<220> FEATURE:
<221> NAME/KEY: misc_feature
<222> LOCATION: (12)..(13)
<223> OTHER INFORMATION: Ribonucleotide
<220> FEATURE:
<221> NAME/KEY: misc_feature
<222> LOCATION: (29)..(29)
<223> OTHER INFORMATION: Ribonucleotide

<400> SEQUENCE: 7
gctcgtctga tgagtccgtg aggacgaaag accgt                              35

<210> SEQ ID NO 8
<211> LENGTH: 35
<212> TYPE: DNA
<213> ORGANISM: Artificial
<220> FEATURE:
<223> OTHER INFORMATION: Description of Artificial Sequence: Nucleozyme
<220> FEATURE:
<221> NAME/KEY: misc_feature
<222> LOCATION: (9)..(9)
<223> OTHER INFORMATION: Ribonucleotide
<220> FEATURE:
<221> NAME/KEY: misc_feature
<222> LOCATION: (12)..(13)
<223> OTHER INFORMATION: Ribonucleotide
<220> FEATURE:
<221> NAME/KEY: misc_feature
<222> LOCATION: (29)..(30)
<223> OTHER INFORMATION: Ribonucleotide

<400> SEQUENCE: 8
gctcgtctga tgagtccgtg aggacgaaag accgt                              35

<210> SEQ ID NO 9
<211> LENGTH: 35
<212> TYPE: DNA
<213> ORGANISM: Artificial
<220> FEATURE:
<223> OTHER INFORMATION: Description of Artificial Sequence: Nucleozyme
<220> FEATURE:
<221> NAME/KEY: misc_feature
<222> LOCATION: (9)..(10)
<223> OTHER INFORMATION: Ribonucleotide
<220> FEATURE:
<221> NAME/KEY: misc_feature
<222> LOCATION: (12)..(13)
<223> OTHER INFORMATION: Ribonucleotide
<220> FEATURE:
<221> NAME/KEY: misc_feature
<222> LOCATION: (30)..(30)
<223> OTHER INFORMATION: Ribonucleotide

<400> SEQUENCE: 9
gctcgtctga tgagtccgtg aggacgaaag accgt                              35

<210> SEQ ID NO 10
<211> LENGTH: 35
<212> TYPE: DNA
<213> ORGANISM: Artificial
<220> FEATURE:
<223> OTHER INFORMATION: Description of Artificial Sequence: Nucleozyme
<220> FEATURE:
<221> NAME/KEY: misc_feature
<222> LOCATION: (9)..(10)
<223> OTHER INFORMATION: Ribonucleotide
<220> FEATURE:
<221> NAME/KEY: misc_feature
<222> LOCATION: (12)..(13)
<223> OTHER INFORMATION: Ribonucleotide
<220> FEATURE:
<221> NAME/KEY: misc_feature
<222> LOCATION: (29)..(30)
```

<223> OTHER INFORMATION: Ribonucleotide

<400> SEQUENCE: 10
gctcgtctga tgagtccgtg aggacgaaag accgt         35

<210> SEQ ID NO 11
<211> LENGTH: 35
<212> TYPE: DNA
<213> ORGANISM: Artificial
<220> FEATURE:
<223> OTHER INFORMATION: Description of Artificial Sequence: Nucleozyme
<220> FEATURE:
<221> NAME/KEY: misc_feature
<222> LOCATION: (9)..(9)
<223> OTHER INFORMATION: 2'-O-methyl-ribonucleotide derivative
<220> FEATURE:
<221> NAME/KEY: misc_feature
<222> LOCATION: (13)..(13)
<223> OTHER INFORMATION: 2'-O-methyl-ribonucleotide derivative

<400> SEQUENCE: 11
gctcgtctga tgagtccgtg aggacgaaag accgt         35

<210> SEQ ID NO 12
<211> LENGTH: 35
<212> TYPE: DNA
<213> ORGANISM: Artificial
<220> FEATURE:
<223> OTHER INFORMATION: Description of Artificial Sequence: Nucleozyme
<220> FEATURE:
<221> NAME/KEY: misc_feature
<222> LOCATION: (9)..(9)
<223> OTHER INFORMATION: 2'-O-methyl ribonucleotide derivative
<220> FEATURE:
<221> NAME/KEY: misc_feature
<222> LOCATION: (13)..(13)
<223> OTHER INFORMATION: 2'-O-methyl ribonucleotide derivative
<220> FEATURE:
<221> NAME/KEY: misc_feature
<222> LOCATION: (29)..(29)
<223> OTHER INFORMATION: 2'-O-methyl ribonucleotide derivative

<400> SEQUENCE: 12
gctcgtctga tgagtccgtg aggacgaaag accgt         35

<210> SEQ ID NO 13
<211> LENGTH: 35
<212> TYPE: DNA
<213> ORGANISM: Artificial
<220> FEATURE:
<223> OTHER INFORMATION: Description of Artificial Sequence: Nucleozyme
<220> FEATURE:
<221> NAME/KEY: misc_feature
<222> LOCATION: (9)..(9)
<223> OTHER INFORMATION: 2'-O-methyl ribonucleotide derivative
<220> FEATURE:
<221> NAME/KEY: misc_feature
<222> LOCATION: (12)..(13)
<223> OTHER INFORMATION: 2'-O-methyl ribonucleotide derivative
<220> FEATURE:
<221> NAME/KEY: misc_feature
<222> LOCATION: (29)..(30)
<223> OTHER INFORMATION: 2'-O-methyl ribonucleotide derivative

<400> SEQUENCE: 13
gctcgtctga tgagtccgtg aggacgaaag accgt         35